United States Patent [19]
Takaya et al.

[11] Patent Number: 4,739,084
[45] Date of Patent: Apr. 19, 1988

[54] RUTHENIUM-PHOSPHINE COMPLEX

[75] Inventors: Hidemasa Takaya; Tetsuo Ohta; Ryoji Noyori, all of Aichi; Nobuo Yamada, Kanagawa; Toshiyuki Takezawa, Saitama; Noboru Sayo, Kanagawa; Takanao Taketomi, Chiba; Hidenori Kumobayashi; Susumu Akutagawa, both of Kanagawa, all of Japan

[73] Assignee: Takasago Perfumery Co., Ltd., Tokyo, Japan

[21] Appl. No.: 38,570

[22] Filed: Apr. 15, 1987

[30] Foreign Application Priority Data

May 13, 1986 [JP] Japan .................................. 61-108888

[51] Int. Cl.$^4$ ........................... C07F 15/00; C07F 9/50
[52] U.S. Cl. ...................................................... 556/21
[58] Field of Search .......................................... 556/21

[56] References Cited

U.S. PATENT DOCUMENTS

| 3,725,489 | 4/1973 | Fuhrmann et al. | 556/21 X |
| 3,748,332 | 7/1973 | Wilkinson | 556/21 X |
| 3,793,355 | 2/1974 | Wilkinson | 556/21 |
| 4,691,037 | 9/1987 | Yoshikawa et al. | 556/21 U X |

*Primary Examiner*—Paul F. Shaver
*Attorney, Agent, or Firm*—Sughrue, Mion, Zinn, Macpeak, and Seas

[57] ABSTRACT

A ruthenium-phosphine complex having a 2,2'-bis(diphenylphosphino)-1,1'-binaphthyl or its derivative as a ligand and carboxyl groups bonded to the ruthenium atom thereof is disclosed. The complex is inexpensive and exhibits excellent performances as a catalyst for various organic syntheses, and particularly for asymmetric hydrogenation.

5 Claims, No Drawings

RUTHENIUM-PHOSPHINE COMPLEX

FIELD OF THE INVENTION

This invention relates to a ruthenium-phosphine complex useful as a catalyst for various organic syntheses, and particularly for asymmetric hydrogenation.

BACKGROUND OF THE INVENTION

Various transition metal complexes have hitherto been employed as catalysts for organic syntheses, and intensive studies have been conducted on syntheses using noble metal complexes as catalysts taking advantages of their stability and easiness in handling though they are expensive. In particular, studies have been directed to asymmetric catalysts to be used in asymmetric syntheses, such as asymmetric isomerization, asymmetric hydrogenation, and the like. Of the reported asymmetric catalysts, metal complexes formed between an olefinic rhodium complex and an optionally active tertiary phosphine are especially well known. Such complexes typically include a rhodium-phosphine complex using 2,2'-bis(diphenylphosphino)-1,1'-binaphthyl (hereinafter abbreviated as BINAP) as a ligand as disclosed in Japanese Patent Application (OPI) No. 61937/80 (the term "OPI" as used herein means "unexamined published application"). One example of application is described in Inoue et al., *Chemistry Letters*, pp. 1007–1008 (1985), in which they obtained citronellol by asymmetric hydrogenation of geraniol or nerol using various rhodium-phosphine catalysts in an optical yield of 66%.

On the other hand, known ruthenium complexes, though there are not so many reports as compared with rhodium complexes, include those having BINAP or 2,2'-bis(di-p-tolylphosphino)-1,1'-binaphthyl (hereinafter abbreviated as T-BINAP) as a ligand, i.e., Ru$_2$Cl$_4$(BINAP)$_2$(NEt$_3$) (wherein Et represents an ethyl group, hereinafter the same) and Ru$_2$Cl$_4$(T-BINAP)$_2$(NEt$_3$), as reported in Ikariya et al, *J. Chem. Soc., Chem. Commun.*, pp. 922 (1985). However, the state-of-the-art ruthenium complexes are not satisfactory in stability as well as asymmetric yield.

Although metallic rhodium provides excellent complex catalysts, it is expensive due to limitations in place and quantity of production. When used as a catalyst component, it forms a large proportion in cost of the catalyst, ultimately resulting in increase in cost of the final commercial products. While metallic ruthenium is cheaper than rhodium and appears promising as a catalyst component for industrial application, it still has problems in its activity to cope with precision reactions and its range of application.

Therefore, it has been keenly demanded to develop a catalyst which is inexpensive, has high activity and durability, and catalyzes asymmetric reactions to attain high optical yields, i.e., to produce reaction products having high optical purity.

SUMMARY OF THE INVENTION

As a result of extensive investigations with the purpose of meeting the above-describe industrial demand, the inventors have discovered a novel ruthenium complex having high catalytic activity, which is usable either for general syntheses when the ligand thereof is optically inactive or for asymmetric syntheses when the ligand thereof is optically active.

The present invention relates to a ruthenium-phosphine complex in which carboxyl groups are bonded to a ruthenium atom, which is represented by formula (I)

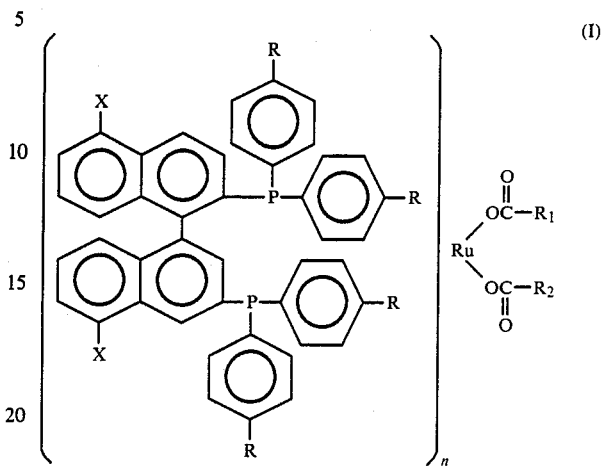

wherein X represents a hydrogen atom, an amino group, an acetylamino group, or a sulfo group; R represents a hydrogen atom or a lower alkyl group (e.g., those having from 1 to 4 carbon atoms); R$_1$ and R$_2$ each represents an alkyl group (e.g., those having from 1 to 9 carbon atoms), a halogenated lower alkyl group (e.g., those having from 1 to 4 carbon atoms; examples of the halogen include fluorine, chlorine, and bromine), a phenyl group, a phenyl group substituted with a lower alkyl group (e.g., those having from 1 to 4 carbon atoms), an α-aminoalkyl group (e.g., those having from 1 to 4 carbon atoms), or an α-aminophenylalkyl group (e.g., those having from 7 to 10 carbon atoms), or R$_1$ and R$_2$ are taken together to form an alkylene group (e.g., those having from 1 to 4 carbon atoms); and n represents 1 or 2.

DETAILED DESCRIPTION OF THE INVENTION

For the sake of brevity, the BINAP derivative moiety in formula (I) as represented by formula

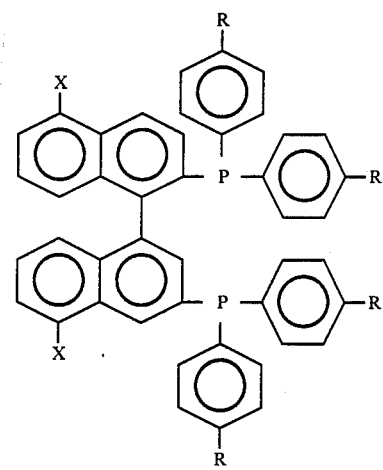

will be hereinafter represented by "L".

The novel ruthenium-phosphine complex of formula (I) according to the present invention can be prepared from Ru$_2$Cl$_4$(L)$_2$(NEt$_3$) as a starting compound.

The starting compound, $Ru_2Cl_4(L)_2(NEt_3)$, can be obtained by the process disclosed in Japanese Patent Application (OPI) No. 63690/86 (corresponding to European Pat. No. 174,057A). Of the starting materials L used herein, those having a sulfo group or an amino group as X can be prepared easily by sulfonation, or nitration followed by reduction, of BINAP, etc., respectively, in a known manner. L in which X is an acetylamino group can be obtained by acetylation of those wherein X is an amino group.

In the preparation of the ruthenium-phosphine complex of the invention, $Ru_2Cl_4(L)_2(NEt_3)$ and a carboxylic acid salt are reacted in an alcohol solvent such as methanol, ethanol, t-butanol, etc. at a temperature of from about 20° to about 110° C. for a period of from 3 to 15 hours. After the solvent is removed by distillation, the desired complex is extracted with a solvent such as diethyl ether, ethanol, etc., and the extract is evaporated to dryness to obtain a crude complex. The resulting crude complex as produced may be used directly as a catalyst for asymmetric hydrogenation or the like reaction, or it may be purified by recrystallization from ethyl acetate, and the like.

Ruthenium-phosphine complexes having any carboxyl group introduced can be obtained by varying the kind of carboxylic acid salt used. Specific examples of the carboxylic acid salts which can be used are sodium acetate, sodium propionate, potassium acetate, silver acetate, sodium butyrate, sodium isobutyrate, sodium monochloroacetate, sodium dichloroacetate, sodium tri-chloroacetate, sodium nonylate, sodium benzoate, sodium p-methylbenzoate, sodium glutarate, sodium octylate, sodium adipate, sodium phthalate, glycine sodium salt, alanine sodium salt, phenylalanine sodium salt, valine sodium salt, leucine sodium salt, isoleucine sodium salt, etc.

Complexes of formula (I) having a trifluoroacetate group are obtained by reacting a diacetate complex of formula (I), $Ru(L)(O_2CCH_3)_2$, as prepared by the abovedescribed process with trifluoroacetic acid in methylene chloride as a solvent at about 25° C. for about 12 hours.

Complexes of formula (I) wherein a 2-equivalent L is coordinated to a ruthenium atom are obtained by reacting $RuHCl(L)_2$ (obtainable by the process disclosed in Japanese Patent Application (OPI) No. 63690/86) with a carboxylic acid salt in a solvent such as methylene chloride.

When an optically active L is used, ruthenium-phosphine complexes having corresponding optically active carboxyl groups bonded thereto can be obtained.

The thus obtained ruthenium-phosphine complex of formula (I) according to the present invention has excellent performance properties as a catalyst for asymmetric hydrogenation or the like reaction. For example, when the complex is applied to asymmetric hydrogenation of allyl alcohols such as geraniol and nerol, it exhibits very high catalytic activity even at room temperature. In some detail, the reaction of geraniol rapidly proceeds in the presence of the complex at a molar concentration of from 1/5000 to 1/50000 based on the geraniol as a substrate to yield a hydrogenation product, i.e., citronellol, at a selectivity reaching almost 100%. The resulting citronellol has an optical purity of from 96 to 98%. To the contrary, the aforesaid known ruthenium complexes described in Japanese Patent Application (OPI) No. 63690/86 are less sufficient in stability, selectivity to citronellol, and solubility in a substrate than the complexes of the invention. In particular, the selectivity to citronellol achieved by the conventional ruthenium complexes is so low that the reaction is accompanied by formation of, as a by-product, dihydrocitronellol having 2 mols of hydrogen added to geraniol or nerol depending on the reaction conditions.

The present invention will now be illustrated in greater detail by way of Examples and Use Examples, but it should be understood that the present invention is not limited thereto. In these examples, all the percents are by weight unless otherwise indicated.

EXAMPLE 1

Preparation of $Ru((-)-BINAP)(O_2CCH_3)_2$ ([2,2'-Bis(diphenylphosphino)-1,1'-binaphthyl]ruthenium-diacetate)

In a 250 ml-volume Schlenk-tube were placed 1.43 g (0.9 mmol) of an $Ru_2Cl_4((-)-BINAP)_2(NEt_3)$ complex which was prepared by the process of Japanese Patent Application (OPI) No. 63690/86 and 3.06 g (37 mmol) of sodium acetate. After the atmosphere was thoroughly displaced with nitrogen, 100 ml of t-butanol was added thereto, followed by heat-refluxing for 12 hours. After completion of the reaction, the t-butanol was removed by distillation under a reduced pressure of 20 mmHg, and the residual solid was extracted twice with 10 ml portions of diethyl ether. The diethyl ether was distilled off to dryness, and the resulting solid was further extracted twice with 10 ml portions of ethanol. The extract was concentrated to dryness to obtain 1.5 g of crude $Ru((-)-BINAP)(O_2CCH_3)_2$. Recrystallization from ethyl acetate gave 0.79 g (yield: 54%) of a yellowish brown solid having a melting point of 180° to 181° C. (with decomposition).

Elemental Analysis for $C_{48}H_{38}O_4P_2Ru$:

|  | Ru | P | C | H |
|---|---|---|---|---|
| Found (%): | 11.85 | 7.28 | 68.35 | 4.61 |
| Calcd. (%): | 12.01 | 7.36 | 68.48 | 4.55 |

The results of instrumental analyses are as follows. The $^1H$ nuclear magnetic resonance spectrum ($^1H$ NMR) was determined with a model of JNM-GX400 (400 MHz) manufactured by JEOL Ltd., and the chemical shift was determined using tetramethylsilane as an internal standard. The $^{31}P$ nuclear magnetic resonance spectrum ($^{31}P$ NMR) was determined with a model of JNM-GX 400 (161 MHz) manufactured by JEOL LTd., and the chemical shift was determined using 85% phosphoric acid as an external standard.

$^{31}P$ NMR (CDCl$_3$) δ ppm: 65.00 (s)

$^1H$ NMR (CDCl$_3$) δ ppm:

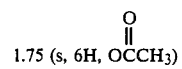

1.75 (s, 6H, OCCH$_3$)

6.5–7.8 (m, 32H, naphthyl ring and phenyl proton)

EXAMPLE 2

Preparation of $Ru((-)-BINAP)(O_2CCF_3)_2$ ([2,2'-Bis(diphenylphosphino)-1,1'-binaphthyl]ruthenium-ditrifluoroacetate)

0.46 g (0.51 mmol) of $Ru((-)-BINAP)(O_2CCH_3)_2$ as prepared in Example 1 was precisely weighed out and placed in a Schlenk-tube with its atmosphere having been replaced with nitrogen. The content was dissolved in 5 ml of oxygen-free methylene chloride to form a uniform solution. To the solution was added 0.09 ml (1.15 mmol) of trifluoroacetic acid having been purified by distillation, followed by stirring at room temperature for 12 hours. After completion of the reaction, the reaction mixture was concentrated to dryness to obtain 0.6 g of a crude complex. The resulting complex was dissolved in 1 ml of toluene, and 5 ml of hexane was added thereto in small portions. The mixture was allowed to stand at room temperature overnight, and the precipitated solid was collected by filtration and dried under reduced pressure (0.2 mmHg) for 10 hours to obtain 0.339 g (yield: 70%) of a purified complex. The resulting complex was identified to be Ru((−)—BINAP)($O_2CCF_3$)$_2$ from the results of elemental analysis and instrumental analyses.

Elemental Analysis for $C_{48}H_{32}F_6O_4P_2Ru$:

|  | Ru | P | C | H |
|---|---|---|---|---|
| Found (%): | 10.47 | 6.43 | 60.89 | 3.57 |
| Calcd. (%): | 10.64 | 6.52 | 60.7 | 3.40 |

$^{31}P$ NMR (CDCl$_3$) δ ppm: 63.016
$^1H$ NMR (CDCl$_3$) δ ppm: 6.1–8.2 (m, 32H)

EXAMPLE 3

Preparation of Ru((−)—T-BINAP)$_2$(O$_2$CCH$_3$)$_2$
(Bis[2,2′-bis(di-p-tolylphosphino)-1,1′-binaphthyl]ruthenium-diacetate)

0.45 g (0.3 mmol) of RuHCl((−)—T-BINAP)$_2$ synthesized by the process of Japanese Patent Application (OPI) No. 63690/86 and 0.11 g (0.66 mmol) of silver acetate were precisely weighed out and placed in a Schlenk-tube, and 5 ml of oxygen-free methylene chloride was added thereto, followed by stirring at room temperature for 12 hours. After completion of the reaction, the reaction mixture was filtered through Celite under a nitrogen stream. The filtrate was concentrated to dryness to obtain 0.57 g of a crude complex. The resulting complex was dissolved in 1 ml of toluene, and 5 ml of hexane was slowly added thereto. The precipitated solid was collected by filtration under a nitrogen stream and dried under reduced pressure (0.5 mmHg) at room temperature to obtain 0.246 g (yield: 52%) of a purified complex. This complex was identified to be Ru((−)—T-BINAP)$_2$(O$_2$CCH$_3$)$_2$ by the results of elemental analysis and instrumental analyses.

Elemental Analysis for $C_{100}H_{86}O_4P_4Ru$:

|  | Ru | P | C | H |
|---|---|---|---|---|
| Found (%): | 6.30 | 7.53 | 76.85 | 5.57 |
| Calcd. (%): | 6.41 | 7.86 | 76.18 | 5.50 |

$^{31}P$ NMR (CDCl$_3$) δ ppm: 63.79
$^1H$ NMR (CDCl$_3$) δ ppm:

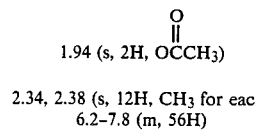

1.94 (s, 2H, OCCH$_3$)

2.34, 2.38 (s, 12H, CH$_3$ for each)
6.2–7.8 (m, 56H)

EXAMPLES 4 TO 17

Complexes were prepared in the same manner as in Examples 1, 2, or 3 except for replacing the respective L and carboxylic acid salt with those shown in Table 1. The preparation was in accordance with Example 1 for Examples 4 to 7, 9 to 13, 15, 16, and 17; Example 2 for Example 8; and Example 3 for Example 14, respectively.

In Table 1, the following abbreviations are used.

| t-Bu: | t-Butyl group |
|---|---|
| i-Pr: | Isopropyl group |
| Ph: | Phenyl group |
| BINAP: | 2,2′-Bis(diphenylphosphino)-1,1′-binaphthyl |
| T-BINAP: | 2,2′-Bis(di-p-tolylphosphino)-1,1′-binaphthyl |
| t-BuBINAP: | 2,2′-Bis(di-p-t-butylphenylphosphino)-1,1′-binaphtyl |
| sulfonated BINAP: | 2,2′-Bis(diphenylphosphino)-5,5′-bis-(sodium sulfonate)-1,1′-naphthyl |
| amino BINAP: | 2,2′-Bis(diphenylphosphino)-5,5′-bis-(amino)-1,1′binaphthyl |
| acetylamino BINAP: | 2,2′-Bis(diphenylphosphino)-5,5′-bis-(acetylamino)-1,1′-binaphthyl |

TABLE 1

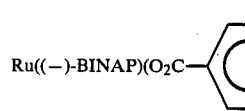

TABLE 1-continued

| Example No. | Complex | Elemental Analysis (%) | | | $^{31}$P NMR δ Value | $^1$H NMR δ Value |
|---|---|---|---|---|---|---|
| | | Element | Found | Calcd. | | |
| | | H | 4.15 | 4.01 | | |
| 9 | Ru((−)-T—BuBINAP)(O$_2$CCH$_3$)$_2$ (for C$_{64}$H$_{70}$O$_4$P$_2$Ru) | Ru | 9.27 | 9.48 | 62.073 | 1.26, 1.24, 1.22, 1.17 (s, 9H for each) |
| | | P | 5.64 | 5.81 | | 1.84 (s, 6H) |
| | | C | 72.26 | 72.09 | | 6.4–7.8 (m, 28H) |
| | | H | 6.74 | 6.62 | | |
| 10 | Ru((+)-amino BINAP)(O$_2$CCH$_3$)$_2$ (for C$_{48}$H$_{40}$N$_2$O$_4$P$_2$Ru) | Ru | 11.43 | 11.59 | 63.174 | 1.88 (s, 6H) |
| | | P | 6.97 | 7.11 | | 3.24 (s, 4H) |
| | | C | 66.30 | 66.13 | | 6.20–7.50 (m, 30H) |
| | | H | 4.73 | 4.62 | | |
| | | N | 3.24 | 3.21 | | |
| 11 | Ru((+)-acetylamino BINAP)— (O$_2$CCH$_3$)$_2$ (for C$_{52}$H$_{44}$N$_2$O$_6$P$_2$Ru) | Ru | 10.44 | 10.57 | 63.832 | 1.92 (s, 6H) |
| | | P | 6.35 | 6.48 | | 2.61 (s, 6H) |
| | | C | 65.48 | 65.34 | | 6.75–7.75 (m, 32H) |
| | | H | 4.79 | 4.64 | | |
| | | N | 2.97 | 2.93 | | |
| 12 | Ru((+)-sulfonated BINAP)- (O$_2$CCH$_3$)$_2$ (for C$_{48}$H$_{36}$O$_{10}$P$_2$RuNa$_2$S$_2$) | Ru | 9.83 | 9.66 | 61.524 | 1.95 (s, H) |
| | | P | 6.11 | 5.92 | | 6.75–8.7 (m, 30H) |
| | | C | 55.03 | 55.12 | | |
| | | H | 3.35 | 3.47 | | |
| 13 | Ru((−)-BINAP)(OC(CH$_2$)$_3$CO) (for C$_{49}$H$_{38}$O$_4$P$_2$Ru) | Ru | 11.69 | 11.84 | 61.61 | 1.20–2.45 (m, 6H) |
| | | P | 7.13 | 7.26 | 61.47 | 6.30–7.90 (m, 32H) |
| | | C | 69.05 | 68.93 | | |
| | | H | 4.57 | 4.49 | | |
| 14 | Ru((−)-T—BINAP)$_2$(O$_2$CCF$_3$)$_2$ (for C$_{100}$H$_{48}$O$_4$F$_6$P$_4$Ru) | Ru | 5.92 | 6.00 | 61.48 | 2.35, 2.48 (s, 12H for each) |
| | | P | 7.28 | 7.35 | | 6.20–7.80 (m, 56H) |
| | | C | 71.48 | 71.30 | | |
| | | H | 4.85 | 4.79 | | |
| 15 | Ru((−)-BINAP)(O$_2$CCHCH$_2$Ph)$_2$ \| NH$_2$ (for C$_{62}$H$_{52}$O$_4$N$_2$P$_2$Ru) | Ru | 9.47 | 9.61 | 50.52 | 2.50–3.10 (m, 10H) |
| | | P | 5.65 | 5.89 | | 6.20–7.90 (m, 42H) |
| | | C | 70.94 | 70.78 | | |
| | | H | 5.17 | 4.98 | | |
| 16 | Ru((−)-BINAP)(O$_2$CCH—i-Pr)$_2$ \| NH$_2$ (for C$_{54}$H$_{52}$O$_4$N$_2$P$_2$Ru) | Ru | 10.41 | 10.57 | 51.07 | 0.28 (d, 6H) |
| | | P | 6.24 | 6.48 | | 0.62 (d, 6H) |
| | | C | 67.95 | 67.84 | | 1.20–1.35 (m, 2H) |
| | | H | 5.73 | 5.48 | | 2.20–2.30 (m, 2H) |
| | | | | | | 2.95 (s, 4H) 6.10–7.90 (m, 32H) |
| 17 | Ru((−)-BINAP)(O$_2$C(CH$_2$)$_7$CH$_3$)$_2$ (for C$_{62}$H$_{66}$O$_4$P$_2$Ru) | Ru | 9.41 | 9.73 | 64.25 | 0.80 (t, 6H) |
| | | P | 5.61 | 5.97 | | 0.84–1.35 (m, 24H) |
| | | C | 72.29 | 71.93 | | 1.92–2.11 (m, 4H) |
| | | H | 6.87 | 6.41 | | 6.46–7.90 (m, 32H) |

USE EXAMPLE 1

A 200 ml-volume autoclave was charged with 62 g (0.4 mol) of geraniol and 75 ml of oxygen-free methanol, and 112 mg (0.13 mmol) of Ru((−)—BINAP)-(O$_2$CCH$_3$)$_2$ as prepared in Example 1 was added thereto under a nitrogen stream to effect hydrogenation at 20° C. for 27 hours under a hydrogen pressure of 30 kg/cm$^2$. After the solvent was distilled off, the residue was subjected to distillation to obtain 61.5 g of a fraction having a boiling point of 108° C./10 mmHg. The resulting fraction was found to contain 98.9% of citronellol by gas chromatography (silica capillary column "OV-101" manufactured by Gasukuro Kogyo Inc.; diameter: 0.25 mm; length: 25 m). The gas chromatography was carried out by increasing the temperature from 100° to 250° C. at a rate of 3° C./min. Optical Rotation, $[\alpha]_D^{25}$ +4.96° (c=31, chloroform).

The resulting citronellol was led to citronellic acid by Jones' oxidation, which was then converted to its amide using R-(+)-(1-naphthyl)ethylamine. The amide was subjected to analysis of diastereomers by high performance liquid chromatography (column: Nucleosil 100-3 produced by Chemco Co., Ltd.; diameter: 4.6 mm; length: 300 mm; eluent: hexane/diethyl ether=7:3 by volume; flow rate: 1 ml/min; detection wavelength: UV 254 nm). As a result, it was found that the starting alcohol was a mixture comprising 97.45% of (R)-(+)-citronellol and 2.55% of (S)-(−)-citronellol. Therefore, the optical yield of this reaction was 94.9%ee.

USE EXAMPLES 2 TO 17

In the same manner as in Use Example 1, geraniol was subjected to asymmetric hydrogenation by using each of the ruthenium-phosphine complexes of the invention as shown in Table 2. The results obtained are also shown in Table 2.

In Table 2, the abbreviations used have the same meanings as described above.

TABLE 2

| Use Example No. | Complex | Substrate/ Catalyst Molar Ratio | Reaction Conditions | | | Reaction Results | | |
|---|---|---|---|---|---|---|---|---|
| | | | Hydrogen Pressure (kg/cm$^2$) | Temperature (°C.) | Time (hr) | Conversion (%) | Asymmetric Yield (%) | Selectivity to Citronellol (%) |
| 2 | Ru((−)-(BINAP)(O$_2$CCF$_3$)$_2$ | 50000/1 | 30 | 20 | 14 | 98.6 | 95.5 | 99.4 |
| 3 | Ru((−)-T—BINAP)$_2$(O$_2$CCH$_3$)$_2$ | 5000/1 | 30 | 20 | 3.7 | 98.7 | 98.5 | 99.4 |

TABLE 2-continued

| Use Example No. | Complex | Substrate/ Catalyst Molar Ratio | Reaction Conditions Hydrogen Pressure (kg/cm²) | Temperature (°C.) | Time (hr) | Reaction Results Conversion (%) | Asymmetric Yield (%) | Selectivity to Citronellol (%) |
|---|---|---|---|---|---|---|---|---|
| 4 | Ru((−)-BINAP)(O₂Ct-Bu)₂ | 1000/1 | 30 | 20 | 50 | 99.3 | 97.1 | 96.9 |
| 5 | Ru((−)-BINAP)(O₂CPh)₂ | 5000/1 | 30 | 20 | 8 | 97.2 | 97.5 | 99.4 |
| 6 | Ru((−)-T—BINAP)(O₂CCH₃)₂ | 10000/1 | 30 | 20 | 8 | 96.2 | 98.8 | 99.8 |
| 7 | Ru((−)-BINAP)(O₂C—C₆H₄—CH₃)₂ | 5000/1 | 30 | 20 | 40 | 97.2 | 96.1 | 99.7 |
| 8 | Ru((−)-BINAP)(O₂CCF₃)₂ | 50000/1 | 30 | 20 | 12 | 99.5 | 97.0 | 99.8 |
| 9 | Ru((−)-t-BuBINAP)(O₂CCH₃)₂ | 10000/1 | 30 | 20 | 5 | 96.3 | 96.3 | 99.7 |
| 10 | Ru-((+)-amino BINAP)(O₂CCH₃)₂ | 5000/1 | 30 | 20 | 48 | 98.2 | 94.1 | 98.7 |
| 11 | Ru-((+)-acetylamino BINAP)-(O₂CCH₃)₂ | 5000/1 | 30 | 20 | 57 | 95.6 | 95.2 | 99.2 |
| 12 | Ru((+)-sulfonated BINAP)-(O₂CCH₃)₂ | 500/1 | 30 | 20 | 32 | 54.5 | 95.0 | 99.3 |
| 13 | Ru((−)-BINAP)(OC(CH₂)₃CO) | 5000/1 | 30 | 20 | 4.5 | 98.5 | 97.5 | 97.5 |
| 14 | Ru((−)-T—BINAP)₂(O₂CCF₃)₂ | 50000/1 | 30 | 20 | 30 | 99.6 | 98.2 | 99.5 |
| 15 | Ru((−)-BINAP)(O₂CCHCH₂Ph)₂ with NH₂ | 5000/1 | 30 | 20 | 23 | 53.6 | 99.7 | 99.6 |
| 16 | Ru((−)-BINAP)(O₂CCH—i-Pr)₂ with NH₂ | 5000/1 | 30 | 20 | 50 | 85.7 | 99.7 | 99.5 |
| 17 | Ru((−)-BINAP)(O₂C(CH₂)₇CH₃)₂ | 2000/1 | 30 | 20 | 50 | 97.8 | 97.5 | 98.9 |

As described above, the present invention provides a novel ruthenium-phosphine complex in which carboxylic groups are bonded to metallic ruthenium. The ruthenium-phosphine complex according to this invention exhibits superior performances as a catalyst for various organic syntheses, and particularly for asymmetric hydrogenation, to accomplish satisfactory results in selective hydrogenation of olefins and catalytic activity from the industrial viewpoint. In addition, the complex of the invention can be prepared at a lower cost as compared with the conventoinal rhodium catalysts, thus making a great contribution to reduction of price of products.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by formula

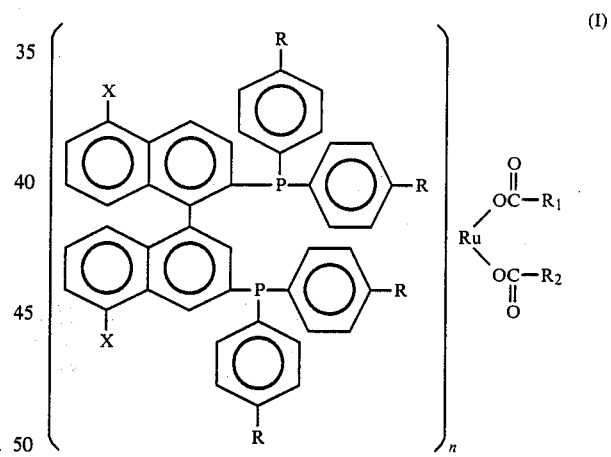

(I)

wherein X represents a hydrogen atom, an amino group, an acetylamino group, or a sulfo group; R represents a hydrogen atom or a lower alkyl group; $R_1$ and $R_2$ each represents an alkyl group, a halogenated lower alkyl group, a phenyl group, a phenyl group substituted with a lower alkyl group, an α-aminoalkyl group, or an α-aminophenylalkyl group, or $R_1$ and $R_2$ are taken together to form an alkylene group; and n represents 1 or 2.

2. [2,2′-Bis(diphenylphosphino)-1,1′-binaphthyl]ruthenium-diacetate, according to claim 1.

3. [2,2′-Bis(diphenylphosphino)-1,1′-binaphthyl]ruthenium-ditrifluoroacetate, according to claim 1.

4. Bis[2,2′-bis(di-p-tolylphosphino)-1,1′-binaphthyl]-ruthenium-diacetate, according to claim 1.

5. Bis[2,2′-bis(di-p-tolylphosphino)-1,1′-binaphthyl]-ruthenium-ditrifluoroacetate, according to claim 1.

UNITED STATES PATENT AND TRADEMARK OFFICE
CERTIFICATE OF CORRECTION

PATENT NO. : 4,739,084

DATED : April 19, 1988

INVENTOR(S) : Hidemasa Takaya et al

It is certified that error appears in the above-indentified patent and that said Letters Patent is hereby corrected as shown below:

In Column 2, lines 6-22 and 47-63, change

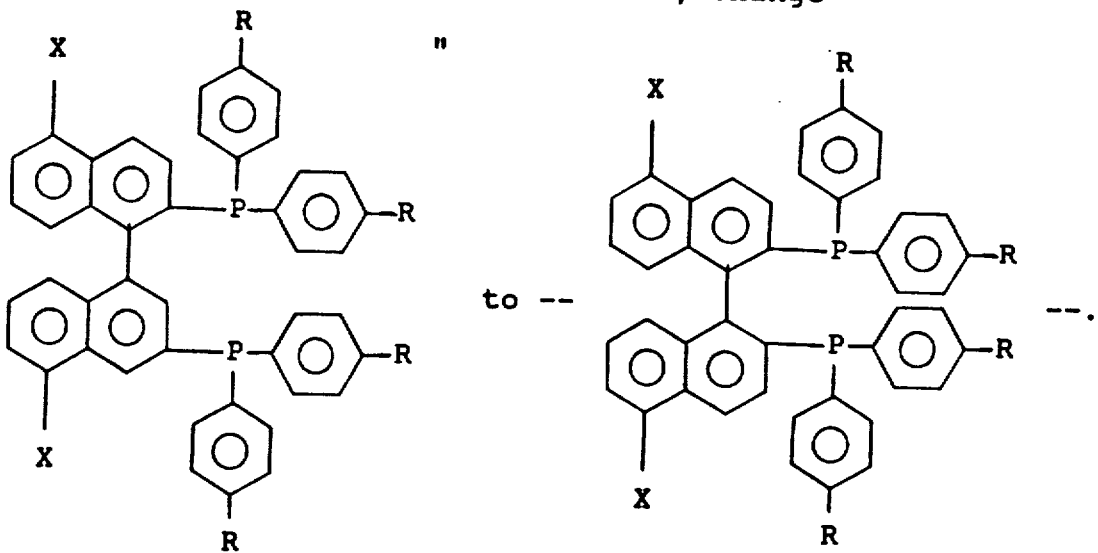

UNITED STATES PATENT AND TRADEMARK OFFICE
CERTIFICATE OF CORRECTION

PATENT NO. : 4,739,084

DATED : April 19, 1988

INVENTOR(S) : Hidemasa Takaya et al

It is certified that error appears in the above-indentified patent and that said Letters Patent is hereby corrected as shown below:

In claim 1, line 3, change

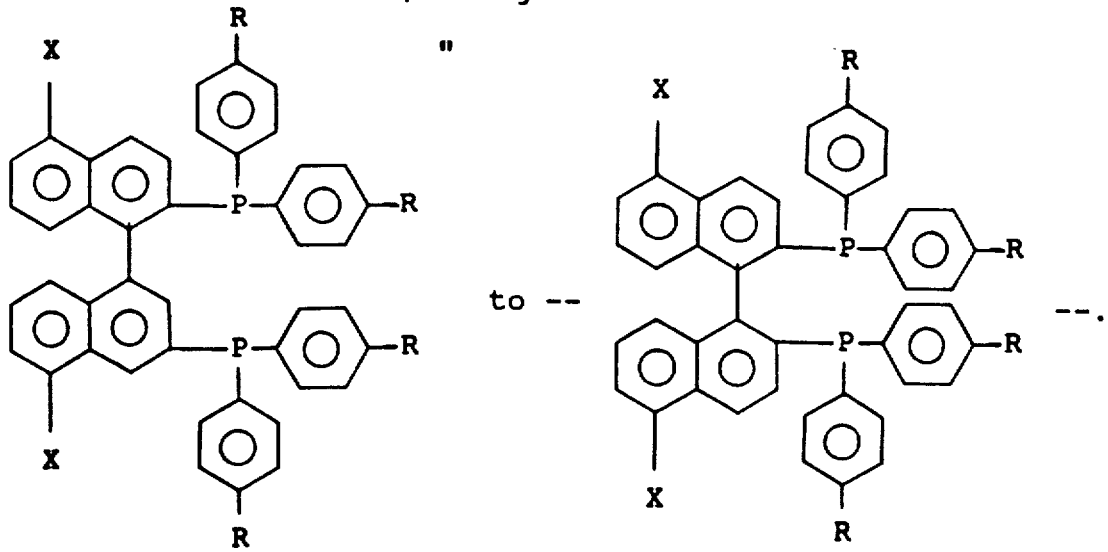

"   to --   --.

Signed and Sealed this

Eighth Day of February, 1994

BRUCE LEHMAN

*Attest:*

*Attesting Officer*     *Commissioner of Patents and Trademarks*